US012203877B2

(12) United States Patent
Salamon et al.

(10) Patent No.: US 12,203,877 B2
(45) Date of Patent: Jan. 21, 2025

(54) CT SYSTEM

(71) Applicant: Fraunhofer-Gesellschaft zur Förderung der angewandten Forschung e.V., Munich (DE)

(72) Inventors: Michael Salamon, Erlangen (DE); Michael Böhnel, Erlangen (DE); Nils Reims, Erlangen (DE); Maurice Jackson, Erlangen (DE); Katrin Zerbe, Erlangen (DE); Ufuk Ergen, Rodgau (DE); Dietmar Koch, Gau-Algesheim (DE); Hans-Thomas Zimmerer, Undenheim (DE); Daniel Christopher Bok, Darmstadt (DE); Özcan Dennis Ak, Mainz (DE)

(73) Assignee: Fraunhofer-Gesellschaft zur Förderung der angewandten Forschung e.V., Munich (DE)

( * ) Notice: Subject to any disclaimer, the term of this patent is extended or adjusted under 35 U.S.C. 154(b) by 315 days.

(21) Appl. No.: 17/585,902

(22) Filed: Jan. 27, 2022

(65) Prior Publication Data

US 2022/0244197 A1 Aug. 4, 2022

(30) Foreign Application Priority Data

Jan. 29, 2021 (EP) ...................... 21154404

(51) Int. Cl.
*G01N 23/046* (2018.01)
*A61B 6/03* (2006.01)

(52) U.S. Cl.
CPC ............ *G01N 23/046* (2013.01); *A61B 6/035* (2013.01)

(58) Field of Classification Search
CPC ....... G01N 23/046; A61B 6/035; G01V 5/226
See application file for complete search history.

(56) References Cited

U.S. PATENT DOCUMENTS

| 4,210,811 | A | 7/1980 | Dennhoven et al. |
| 7,545,905 | B2 | 6/2009 | Muenker et al. |
| 2006/0126772 | A1 | 6/2006 | Hu et al. |
| 2008/0089466 | A1 | 4/2008 | Munker et al. |

(Continued)

FOREIGN PATENT DOCUMENTS

| JP | 2003065973 A | 3/2003 |
| JP | 2006038836 A | 2/2006 |

(Continued)

OTHER PUBLICATIONS

Zabler, S. , et al., "Industrial X-ray Computed Tomography Scanner", Handbook of X-ray Imaging: Physics and Technology, CRC Press, 2017.

(Continued)

*Primary Examiner* — David P Porta
*Assistant Examiner* — Meenakshi S Sahu
(74) *Attorney, Agent, or Firm* — PERKINS COIE LLP; Michael A. Glenn

(57) ABSTRACT

CT system including: an X-ray source and an X-ray detector arranged opposite the X-ray source, wherein the X-ray detector and the X-ray source may be mutually rotated around at least one rotation center through a rotator, wherein the distances between the at least one rotation center and the X-ray source and between the at least one rotation center and the X-ray detector are different.

20 Claims, 6 Drawing Sheets

(56) References Cited

U.S. PATENT DOCUMENTS

| | | | |
|---|---|---|---|
| 2012/0087470 A1 | 4/2012 | Omote et al. | |
| 2016/0084775 A1 | 3/2016 | Kang et al. | |
| 2019/0353601 A1 | 11/2019 | Sauerwein et al. | |
| 2020/0100736 A1 | 4/2020 | Lemer | |
| 2020/0326289 A1* | 10/2020 | Takeda | G06T 15/08 |

FOREIGN PATENT DOCUMENTS

| | | | |
|---|---|---|---|
| JP | 2006105787 A | 4/2006 | |
| JP | 2007041002 A | 2/2007 | |
| JP | 2008064758 A | 3/2008 | |
| JP | 2008122337 A | 5/2008 | |
| JP | 2012080963 A | 4/2012 | |
| JP | 2020505613 A | 2/2020 | |
| WO | WO-2020133586 A1 * | 7/2020 | G21F 3/00 |

OTHER PUBLICATIONS

Salamon, Michael, "XXL CT capabilities for the inspection of modern Electric Vehicles", International Symposium on Digital Industrial Radiology and Computed Tomography, 2019.

HCVG Gantry inspection system, Available: https://www.smithsdetection.com/products/hcvg/. [Access on Apr. 2, 2020]., printout of website attached, accessed Mar. 1, 2022.

HI-SCAN 6040 CTiX, Smith Detection, [Online]. Available: https://www.smithsdetection.com/products/hi-scan-6040-ctix/. [Access on Apr. 2, 2020], printout of website attached, accessed Mar. 1, 2022.

* cited by examiner

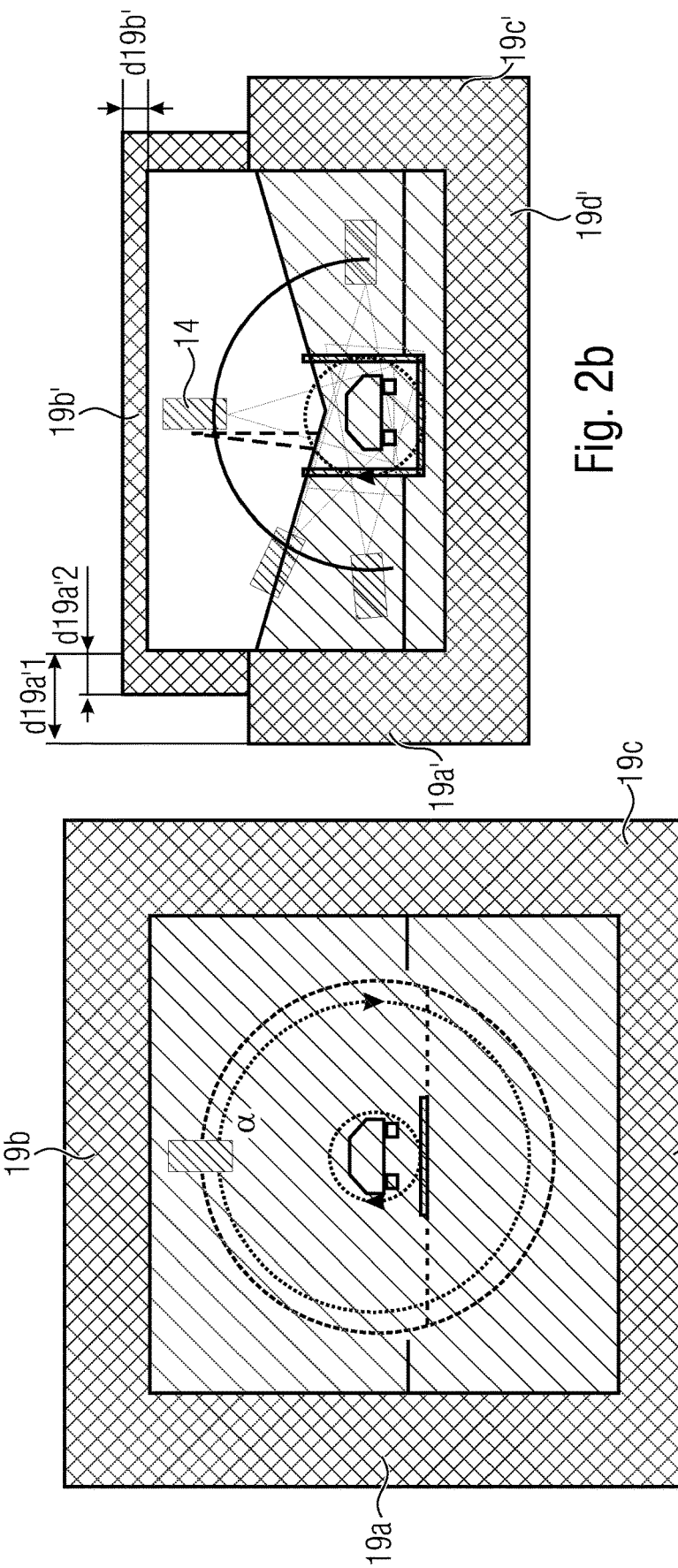

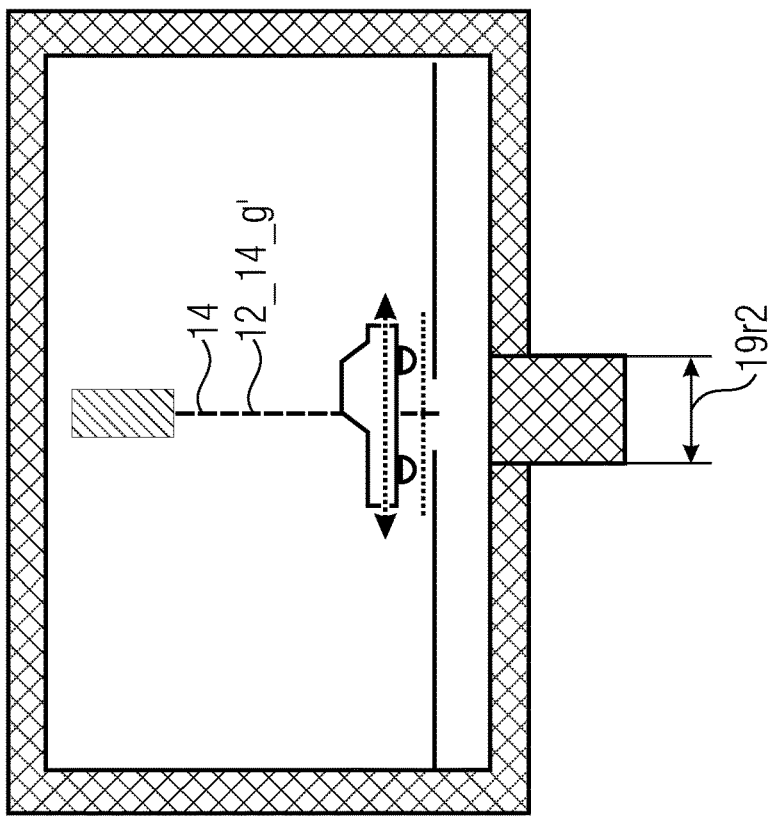
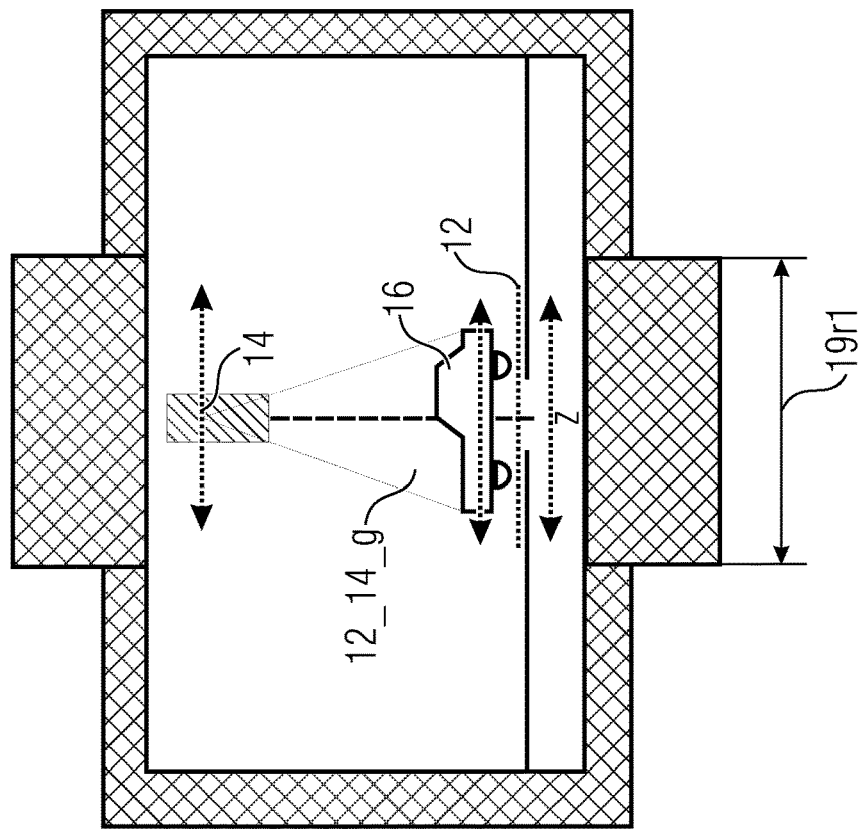
Fig. 3a
Fig. 3b

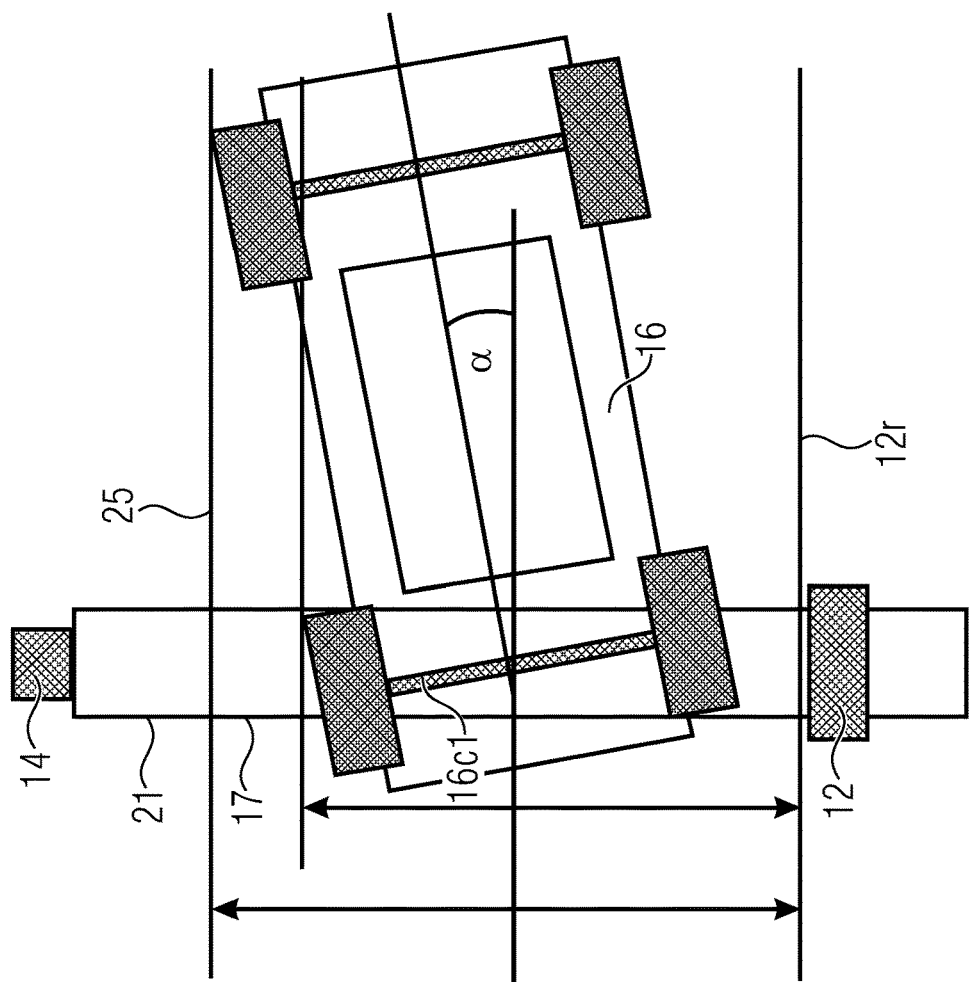
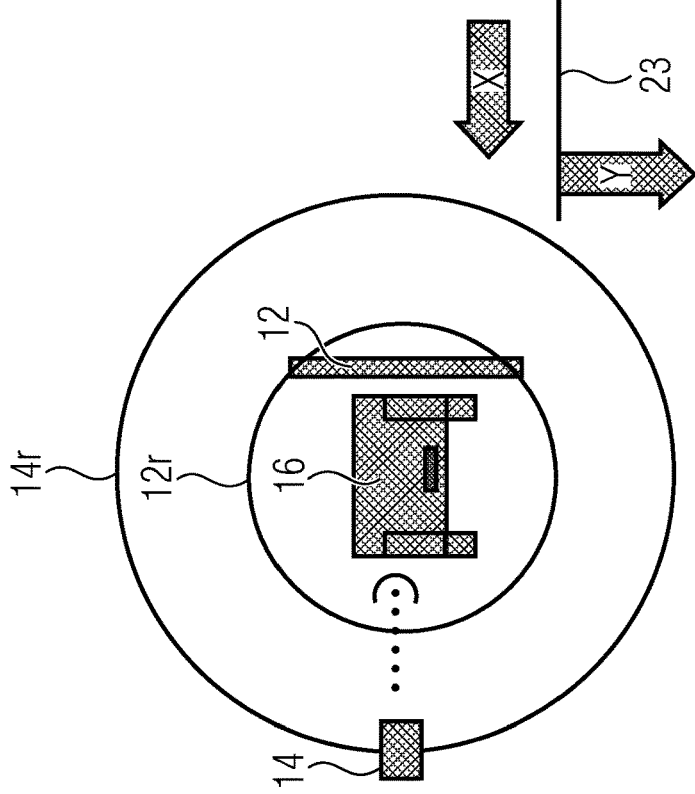
Fig. 4b
Fig. 4c

CT SYSTEM

CROSS-REFERENCE TO RELATED APPLICATIONS

This application claims priority from European Patent Application No. 21154404.4, which was filed on Jan. 29, 2021, and is incorporated herein in its entirety by reference.

Embodiments of the present invention concern a CT system, in particular a CT system for tomographing very large and/or long objects, such as vehicles in their natural position (road position), while maintaining a high resolution.

BACKGROUND OF THE INVENTION

Computer tomography (CT) has established itself in many industrial applications as a valuable tool to obtain information about the internal geometry, material composition, and possible defects in components. In addition, CT is increasingly used for dimensional measurements, e.g. geometry reconstruction, where imagining involves high geometric precision. For a long time, the component size was a limiting factor. Only a few years ago, the three-dimensional capturing of large-scale objects, such as entire vehicles, became possible with adequate spatial resolution, as demonstrated in the work around the XXL CT at Fraunhofer EZRT [1], [2]. To optimally image the large-format objects to be measured, the radiation penetration direction and the associated materials thickness to be penetrated by radiation are decisive factors. Radiation penetration along the longitudinal axis of the object should be avoided, since X-ray sources available on the market are not capable of sufficiently permeating objects in a range of meters. This can be seen particularly clearly in the example of an electric vehicle in the region of the high-voltage storage unit. Due to the lack of permeation, vehicle details cannot be detected in this region. For this reason, vehicles such as cars, SUVs, or even airplanes are now scanned in XXL CT in an upright position in a suitable rack. This significantly increases the scan quality.

To further establish the scanning technology, the usability has to be improved, and the time-consuming and highly distorting upright positioning of the vehicles is to be avoided. Due to the gravitational effect being changed by 90° (compared to the native road position) and the associated material stresses alone, the results can only be used to a limited extent for many questions (e.g. target/actual comparison between a CAD model and a scanned vehicle). In addition, the erection process needs considerable personal and temporal effort for emptying the operating fluids and securing the vehicle. The integrity of the vehicle can only be ensured to a limited extent, which is why the process cannot be carried out on vehicles for series production applications.

To avoid the problems mentioned, it is obvious to use a gantry CT system that rotates 360° around the measurement object, as has been used in medical science for a long time. In the industrial field, e.g., such systems are used in the baggage inspection [3]. However, simply adapting this technology to large-format objects is not possible. This is due to the following reasons. In order to have sufficient permeation capability, a high-energy X-ray source with a radiation beam energy of >1 MeV has to be used. Due to the emission characteristic of such high-energy sources, the focus-to-detector distance is ≥10 m, even if only vehicles with a maximum cross section of 3 m are to be scanned. This results in a very large construction effort so as to construct a ring with a diameter of approximately 10-12 m that is sufficiently precise, heavy load-capable and can be rotated around 360°. Another disadvantage is the needed provision of a correspondingly large measurement hall, including sufficiently thick shielding to ensure radiation protection. The field of border control and security also uses so-called gantry portals to check vehicles and containers [4]. However, these differ fundamentally from the system presented here. The systems available on the market are not rotating systems, i.e. it is not possible to capture the full 3D image of the test objects. It is only possible to radiograph the object from two viewing directions by placing two source detector pairs at a fixed angle to each other. Even though some patents describe a rotating gantry, they have not yet been realized and used in practice. Furthermore, these systems are optimized with respect to cycle time. The achievable spatial resolution is therefore not the main concern, which is why the solutions cannot be used for the application purpose of non-destructive testing. With the invention described herein, vehicles or other large and/or elongate objects may be captured with a high resolution as well as very efficiently in their native position (its road position in the case of a car) in two and/or three dimensions. On the one hand, the difficulties of the upright scanning process are avoided. On the other hand, compared to the adaption of a classical medical gantry approach (360° ring), a reduction of complexity and efforts with respect to construction, manufacturing, handling, and radiation protection is possible. Therefore, there is a need for an improved concept.

There are already some conventional approaches:
Tomography system for scanning very large and/or long objects (XXL CT)→limited object length, bad image quality in highly-absorbing areas, cf. XXL CT capabilities for the inspection of modern electric vehicles https://www.ndt.net/search/docs.php3?id=24754
Tomography system for upright scanning of very large and/or long objects (XXL CT)→no natural position (gravity, effort, rack), cf. XXL CT capabilities for the inspection of modern electric vehicles https://www.ndt.net/search/docs.php3?id=24754
Conventional small gantry systems, based on medical gantry systems, e.g. baggage CT gantry scanner→360°, limited object size (cf. https://www.smithsdetection.com/products/hi-scan-6040-ctix/)
Truck gantry portal→tomography is not possible (cf. gantry inspection system https://www.smithsdetection.com/products/hcvg/)
Security gantry portal→very similar to the implementation, however, not specified with respect to the resolution. The realization for the security application purpose needs only a coarse spatial resolution. Our concept enables the optimization of the arrangement of the components up to a maximum resolution in the sub-millimeter range above the described conventional technology, cf. US 2006/0126772 A1

SUMMARY

According to an embodiment, a CT system may have: an X-ray source; and an X-ray detector arranged opposite the X-ray source, wherein the X-ray detector and the X-ray source are rotatable around at least one rotation center through a rotation means, wherein the distances between the at least one rotation center and the X-ray source and between the at least one rotation center and the X-ray detector differ from each other by at least factor 2.

Embodiments of the present invention provide a CT system with a (high-energy) X-ray source and an X-ray detector arranged opposite the X-ray source. The X-ray detector and the X-ray source are mutually rotatable around at least one rotation center (stationary point, or axis of rotation, extending in the z-direction).

The distances between the at least one rotation center and the X-ray source as well as between the at least one rotation center and the X-ray detector are different. For example, the distances can differ at least by factor 2. According to embodiments, the rotation means comprises a means for rotation and a suspension of the X-ray detector and the X-ray source. According to embodiments, the suspension, or the arrangement of the X-ray detector and the X-ray source with respect to the at least one rotation center in general, is designed such that an asymmetrical arrangement of the X-ray source and the X-ray detector with respect to an object to be penetrated by radiation arises. Here, according to embodiments, the object may be arranged between the X-ray source and the X-ray detector such that the at least one rotation center, or the rotation axis, extends through the object to be penetrated by radiation.

Embodiments of the present invention are based on the finding that a simultaneously high resolution may be achieved through the asynchronous arrangement around the rotation center even if the overall installation space is not excessively increased. In detail, by mounting the radiation source on a cantilever, a significantly smaller gantry ring diameter is used overall if, e.g., the radiation detector is guided on a shorter cantilever, or on a smaller radius. In particular, this also enables the use of low-cost standard components.

According to further embodiments, when assuming the rotation to be reduced to only 180°+opening angle (180° in general, a sum of 180° and the fan angle, around an angle of between 0° and 120° to 180°, around an angle of between 0° and 150° to 210°, around an angle of between 0° and 120° to 240°, around an angle of <240°, or around an angle of <360°, the construction effort of a high-resolution CT system for very large objects may be significantly reduced with respect to costs, installation space, complexity. Thus, possible applications are XXL CTs, gantry CTs, non-destructive testing, e.g. in automotive engineering, such as by means of portal CTs. Embodiments as characterized above further enable the following advantages:
1. Native position (road position) of the measurement objects during scanning
2. No upright position
    a. Less requirements with respect to time and personnel
    b. No rack needed
    c. Gravity position
        i. Deformation
        ii. Liquids
3. Simpler wiring (no slip rings)
4. Easy accessibility to the object since there is no need for a giant recess in the floor or an object-lifting device
5. Smaller hall, easier radiation protection
6. Easier assembly (e.g. bearings are standard components from wind power engineering), no need for insertion through a ceiling
7. Less radiation protection in the ceiling area by limiting the rotation to 180°+opening angle instead of 360° (limited-angle approach)
8. Less radiation protection along z through object feed Easier accessibility since the ring is smaller (only the cantilever has the full distance of 12 m).

According to further embodiments, the distance between the one rotation center and the X-ray source is larger than the distance between the at least one rotation center and the X-ray detector. For example, the distances may differ at least by the factor 2, at least by the factor 3, or at least by the factor 4. For example, when assuming the distance between the rotation center and the X-ray source to be 8 m, the distance between the rotation center and the X-ray detector is 2 m, for example. According to embodiments, the distance between the at least one rotation center and the X-ray detector is a maximum object cross section of an object to be penetrated by radiation, e.g., 2 m in the case of a car. According to further embodiments, the distance is smaller than a maximum object cross section.

According to embodiments, a high-energy radiation source such as a linear accelerator is used. In particular, when irradiating large objects, or objects with high-density components, this has advantages with respect to the spatial resolution.

According to embodiments, the X-ray detector is realized as a line detector or surface detector extending tangentially along a rotation circle of the CT system. According to embodiments, the X-ray detector may also be a curved line detector or curved surface detector extending along a rotation circle of the CT system.

According to an embodiment, the rotation means includes a rigid mount (mount in a reduced rotation circle), wherein the rigid mount mounts the X-ray detector along its movement around a rotation axis. According to further embodiments, the rotation means includes a cantilever in which the X-ray source is fixed, wherein the cantilever is rotatable along a (further) rotation circle, or the X-ray source rotates along this further rotation circle.

According to an embodiment, the CT system comprises an object holder or a moveable object holder (an object holder moveable in the z-direction). The moveable object holder is configured to be moved along a feed direction (z-direction) extending, e.g., perpendicularly across rotation circles. According to an embodiment, the object holder may comprise the form of a stage. According to an embodiment, the object holder is configured to record objects larger than 1×1×1 meters, larger than 2×2×1 meters, or larger than 2×2×2 meters or 1.5×1.5×1 meters.

According to an embodiment, the CT system may be mobile, e.g. a mobile portal CT. According to embodiments, it would be conceivable to provide mobile radiation protection blocks. Due to the limited rotation radius, e.g., a setup of these radiation protection blocks next to the same is sufficient. According to embodiments, the object to be penetrated by radiation, e.g. the car or truck, may be directly penetrated by radiation on the road surface.

According to embodiments, the CT system can have a movable holder that is configured to be moved along a feed direction which extends, for example, perpendicular to the surface of the revolution of the x-ray detector and the x-ray source rotating around the at least one rotation center. This means that an elongated object can be scanned through its length direction, while the object is moved through the gantry/surface evolution. According to embodiments, the feed direction extends angled by an angle to the surface of revolution. The angle may amount, for example, to 95° or 90° or 85°. In general, the angle lies in a range between 75° or between 80 and 85°, or between 75 and 89°. This has the beneficial effect that components of the object extending in parallel to the rotational surface, e.g., an axis of a vehicle, can be scanned obliquely, so that the resolution of the object can be enhanced. Note, according to embodiments, the feed direction extends through the at least one rotational axis. This holds true when the feed direction is perpendicular to the surface of revolution or angled to the surface of revolution. This oblique feed direction can be achieved when the movement has two components, e.g., an x and a z component. As discussed above, the result is that, according to embodiments, a component of interest of the object is angled with respect to the surface of revolution, such that same can be x-rayed.

BRIEF DESCRIPTION OF THE DRAWINGS

Embodiments of the present invention will be detailed subsequently referring to the appended drawings, in which:

FIG. 2a shows a possibility for shielding in the case of a conventional structure;

FIG. 2b shows a schematic illustration of the reduction of the radiation protection shielding with the help of embodiments;

FIGS. 3a and 3b show schematic illustrations of a longitudinal section through an overall vehicle CT (FIG. 3a with a moveable imaging system, FIG. 3b with a fixed imaging system around a moveable object); and FIG. 4a-4c show schematic illustrations of an object to be scanned moving through a CT system (FIG. 4a having a conventional movement direction, FIGS. 4b and 4c having a movement enabling an improved scanning performance) according to embodiments.

DETAILED DESCRIPTION OF THE INVENTION

Figure 1A:
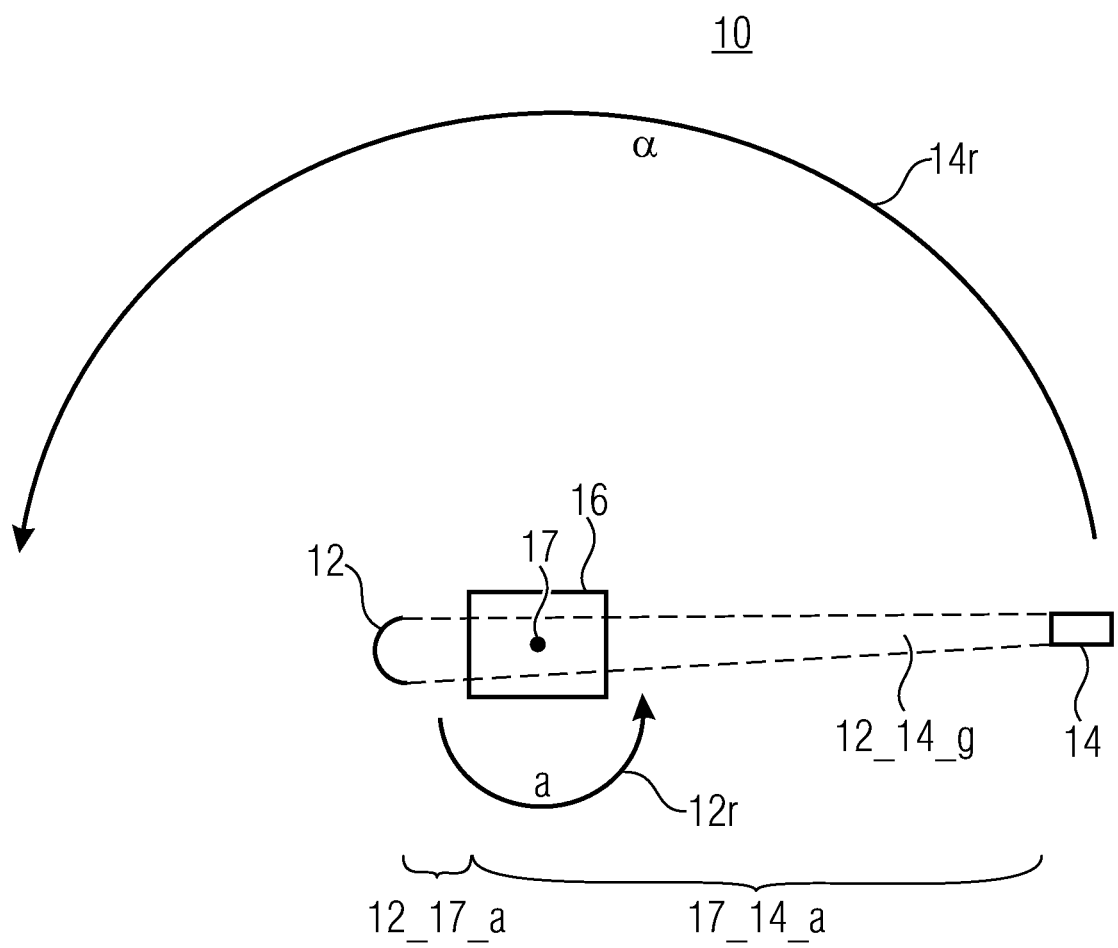
FIG. 1a shows a schematic illustration of a CT system according to a base embodiment.

Before embodiments of the present invention are subsequently explained on the basis of the accompanying drawings, it is to be noted that elements and structures having the same effect are denoted with the same reference numerals so that their description can be applied to each other and/or is mutually interchangeable.

FIG. 1a shows a CT system 10 with a radiation source 14 and a radiation detector 12. The radiation source 14 and the radiation detector 12 are arranged opposite each other so that the radiation geometry 12_14_g arises during operation. The CT system 10 is used to penetrate the object 16 by radiation, said object being assumed to be very large, e.g. having dimensions of 1×1×1 meters or 2×2×1 meters or 2×2×2 meters and 1.5×1.5×1 meters. An example for the object 16 would be a car or a truck. The object is to be fully penetrated by radiation.

The arrangements of the detector 12 and the radiation source 14 are rotatable, e.g., in this case around 180°, as is illustrated on the basis of the angle α. The angle α is drawn in for two different rotation circles 12r and 14r. 12r belongs to the rotation trajectory of the detector 12, whereas 14r belongs to the rotation trajectory of the radiation source 14. In this case, the rotation is performed around the rotation center 17. According to embodiments, the rotation center 17 may be arranged such that the rotation axis extends through the object 16. Consequently, the CT system, or in particular the components 14 and 12 of the CT system, rotate(s) around the object 16. The rotation is realized by means of a rotation means, e.g., which may comprise a mount, connection elements in the form of a C-arm or the like, and a drive. The rotation means is mentioned here only by way of example and is not illustrated.

The detector 12 and the radiation source 14 are arranged such that the distances 12_17_a and 17_14_a arise between the detector 12 and the rotation center 17 and between the rotation center 17 and the radiation source 14, respectively.

According to this base embodiment, the distance 12_17_a differs from the distance 17_14_a. For example, the distance 17_14_a is larger than the distance 12_17_a. An exemplary size ratio is 1:2 or 1:4, although any other size ratios, such as 1:1.5, would be theoretically conceivable. What arises through this is an asymmetrical arrangement of the radiation detector 12 with respect to the rotation center 17, or the position of the object 16, compared to the position of the radiation source 14 with respect to the rotation center 17, or the object 16. On the basis of this asymmetrical arrangement, the radius of the movement trajectory of the detector 12 (cf. 12r) is significantly smaller than the radius of the radiation source 14 (cf. 14r). When assuming the radiation source 14 to rotate above the object 16 and the detector 12 to rotate below the object 16 (both around 180°, for example), the geometry of the CT system may be improved by not keeping the same distance to all sides, however, while ensuring that the overall CT system may penetrate the object 16 by radiation and thereby covers practically all solid angles needed for a reconstruction, while still allowing a high spatial resolution.

The above embodiments assumed that the distance 12_17_a is smaller than the distance 17_14_a, which is particularly advantageous with respect to the spatial resolution, but not mandatory. Subsequently, the detailed background and possible further embodiments, or implementation details, are explained. Embodiments of the present invention are based on a vertically rotating gantry system, as is also used in the medical field. The imaging system 10 mounted on the rotating gantry and consisting of the opposite components radiation source 14 and detector 12 captures during the rotation movement the test object from the many observation angles (for example ≥100). Embodiments use two facts: (1) the asymmetrical arrangement of the radiation source and the detector around the rotation center with a mount ring having a diameter adapted to the dimensions of the object, and (2) the fact that a rotation around 180°+ opening angle of the radiation geometry is sufficient for fully scanning the object.

This enables a special mounting of the imaging system so as to achieve the needed large trajectories, which is subsequently described on the basis of an embodiment in more detail.

For example, the focus-detector distance for objects of the size of a car is approximately 10 m. In this case, the distance between the radiation source and the rotation center may be approximately 8 m, the distance between the object and the rotation center may be approximately 2 m. This clearly distinguishes the system from the almost symmetrical small rotating gantry systems for medical and technical applications. The accuracy requirement in the positioning of the components is not isotropic so that the requirement on the side of the detector is significantly larger (+/−200 μm) than on the side of the radiation source (+/−800 μm). According to embodiments, the radius of the detector 12 may amount to two or three meters (generally in the range between 1 and 4 meters), while the radius of the source 14 may amount to 8 to 10 meters. Starting from this, the cantilever by use of which the source is coupled to the detector 12 can have a length between 5 or 7 meters (in general, between 3 or 10 meters).

Instead of a gantry ring with a diameter of 10 m, a gantry ring with a radius=object-detector distance (here approximately 2 m), or maximum object cross section, is used. This simplifies the construction for a CT scanner significantly, in particular for the high precision needed (in particular on the side of the detector). For high positional fidelity, the detector may be placed in close proximity to the supporting ring structure or directly to the supporting ring structure. Background is that the fixing of the detector to the ring without leveling arm avoids effects caused by a leveling arm, like a deflection of the leveling arm resulting in a displacement of the detector and drawbacks regarding resolution. For example, highly precise bearings from wind turbine engineering may be used for the ring. In order to realize the needed focus-detector distance of 10 m, the linear accelerator is mounted on a cantilever that is connected to the ring and that is characteristic for the invention. Due to the anisotropic accuracy requirements specified in the invention, the leverage effect on the accuracy dimensions resulting from the cantilever position may be tolerated. With the aid of this feature, the mechanical positioning unit (gantry) may be implemented considerably more efficiently and therefore less expensively than when using a symmetrical variant with uniform precision requirements. In addition, further inaccuracies resulting from the structure may be compensated for by means of a computing unit during volume reconstruction.

In addition, the presented system has a rotation range α with 180°<α<360°. Through this, the needed installation space is reduced depending on to the α used. In addition, the operation of the components on the ring is facilitated. For example, it is not necessary to introduce the power supply or signal supply via slip rings or over-the-air technology.

Figure 1C:
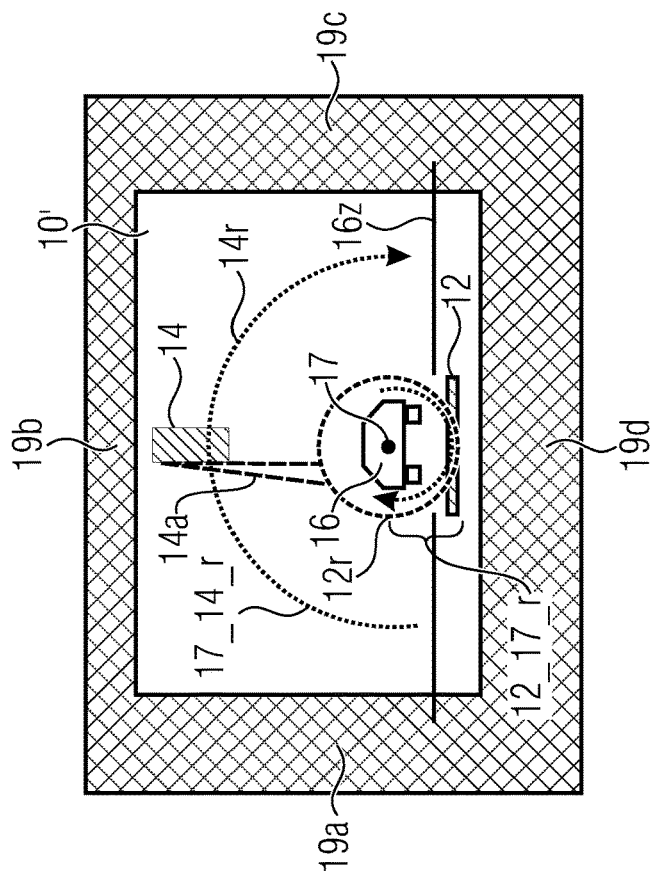
FIGS. 1b and 1c show schematic illustrations of a structure of an overall vehicle CT with a symmetrical arrangement of the components in the large ring (illustration b) and with an asymmetrical arrangement with a cantilever for the radiation source according to embodiments (illustration c)
Figure 1B:
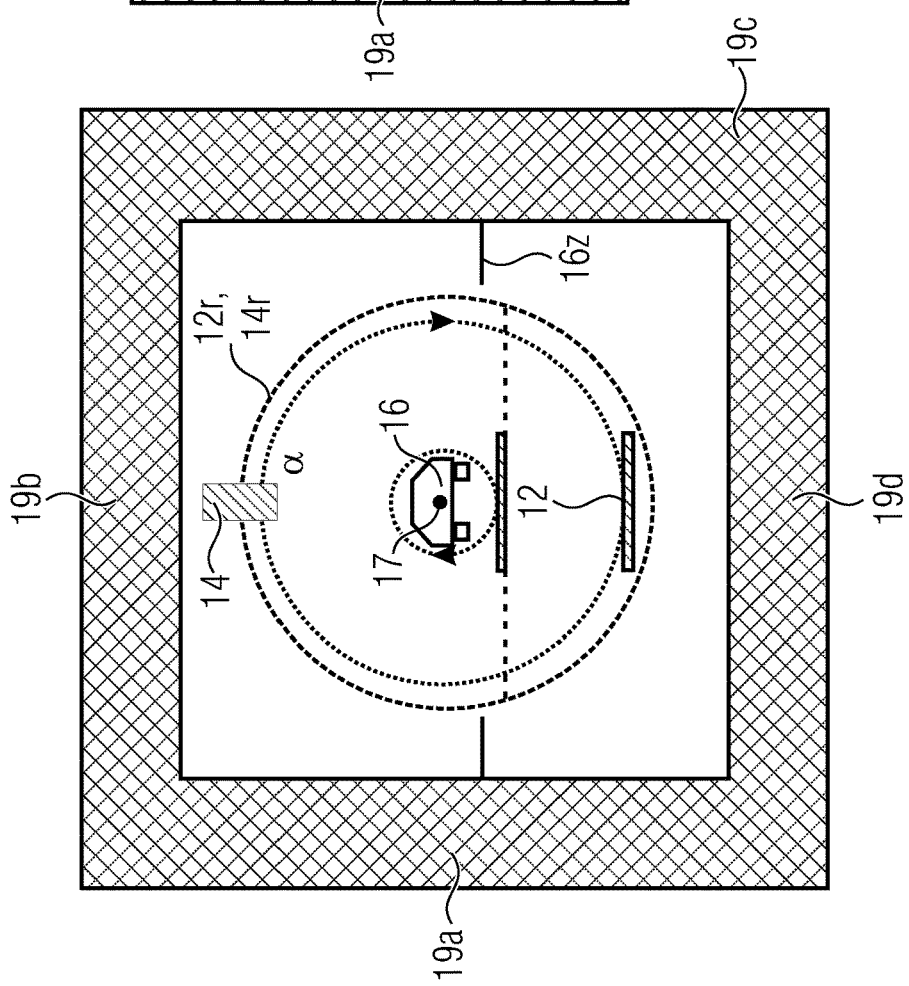

With reference to FIGS. 1b and 1c, the advantage over conventional structures is described in the following. The combination of the omission of a complete 360° rotation with the use of the cantilever, which causes an asymmetrical arrangement, enables a significantly reduced installation cross section, as is shown on the basis of FIG. 1c.

FIG. 1b shows a conventional structure of an X-ray system/CT system for an object, such as a car 16. Here, the rotation point is again denoted with the reference numeral 17 and also extends through the object 16. The detector 12 and the radiation source 14 rotate on the trajectory 12r and 14r, respectively, around the rotation center 17. The trajectories 12r and 14r are identical, namely a closed circular trajectory. In this respect, a rotation angle α of 360° arises. As a result of the total rotation, the object 16 has to be arranged with an object receptacle (not shown) centered in the rotation circle 12r and 14r, respectively. In a possible implementation, the object 16, e.g. a vehicle, would have to be lifted onto a stage, and the elements 12 and 14 would have to be rotated around the same along the rotation trajectory 12r and 14r, respectively. Due to the needed full rotation and the identical rotation trajectories of the elements 12 and 14, cf. 12r and 14r, respectively, a considerable amount of space is needed. The further disadvantage is the arrangement of radiation protection elements that have to be implemented around the CT system. The radiation protection arrangement is denoted with the reference numerals 19a-d and is of equal thickness on all four sides, since the same radiation exposure arises on all sides during the 360° rotation.

An improvement is achieved now in FIG. 1c. In turn, FIG. 1c shows an arrangement of a CT system 10' with the radiation source 14 and the radiation detector 12 rotation around the rotation center 17. This results in a rotation around the rotation trajectory 12r. In turn, the rotation center 17 extends through the object 16. In the arrangement 10', the detector 12 is mounted similarly to the detector 12 of FIG. 2a, e.g. in a type of gantry or tube, wherein the radius 12_17_r are reduced significantly. On the other hand, the radiation source 14 is guided via a cantilever 14a on a further trajectory 14r. Here, the rotation trajectories 14r and 12r are concentric since they have a common rotation center 17, but their radius is different. The radius of the rotation trajectory 14r is denoted with the reference numeral 17_14_r.

The combination of the omission of a full 360° rotation with the use of the cantilever enables a significantly reduced cross section of the structure. Thus, the radiation protection hall has only half the cross section, as is shown in FIG. 1b, and the accessibility to the measurement area is essentially only slightly constricted in the area of the detector. At this point, it is to be noted that the accessibility to the object 16 is illustrated in the respective embodiments on the basis of the lines 16z and FIGS. 1b and 1c. As can be seen, in the embodiment of FIG. 1c, the accessibility is increased significantly. It is a further advantage that, due to the limited rotation range, large parts of the sidewalls and particularly the hall ceiling are not irradiated and that, according to radiation protection aspects, they have to be implemented less massively, as is shown in FIGS. 2a, 2b (e.g. here in a line-type manner with a width of 4 m).

For example, mounting is carried out with a gantry structure (mounting on a maximum or mean trajectory).

In other words, mounting the detector 12 is here carried out in the area of the object 16, wherein the cantilever 14a supports the accelerator 14.

FIG. 2a assumes the situation according to the embodiment of FIG. 1b, whereas FIG. 2b assumes the structural situation of FIG. 1c. On the basis of the hatched area, the zone with a direct irradiation is defined, on the basis of which the radiation protection objects 19a-19d have to be dimensioned. All zones with a direct irradiation are dimensioned with a significantly larger shielding than the periphery areas. In the embodiment of FIG. 1c, or FIG. 2b, this results in a changed shielding situation. For example, in FIG. 1c, compared to the shielding regions 19a', 19c' and 19b', the shielding region 19b' is implemented with a reduced thickness. In the embodiment of FIG. 2d, further optimizations have been carried out, wherein parts of the shielding regions 19a' have a reduced diameter. The diameters are each denoted with the reference numerals d19a'1, d19a'2 and d19b'. Here, e.g., the lower area associated with the direct radiation zone (opposite the radiation source 14) is provided with a thicker wall thickness d19a'1 than the upper area of 19a' (cf. d19a'2). In other words, this wall thickness d19a'2 with the reduced thickness is used in the wall area above the dashed area. Through the concept, the thickness of the ceiling (cf. d19b'), which is complex from a supporting structure point of view, may be minimized significantly.

In addition to the rotational movement, according to embodiments, a feeding of the measurement area may be carried out. In the case of long objects, the full object length may never be captured during a rotation since the height of the detector is too small. To this end, the invention provides a translational movement in the longitudinal direction of the measurement object through the measurement field spanned by the components in one or several planes. In this case, the object is secured on a moveable object stage that is easily penetrated by radiation, and is driven step-wise and continuously through the radiation. The stage may contain degrees of freedom for the re-positioning of the vehicle/object in the scanning area so as to achieve an optimum radiation penetration length in areas of higher density such as in the transmission or the motor block.

According to embodiments, through the translation of the object (in the form of the object stage) instead of the translation of the imaging system, the radiation protection effort for the hall may be further reduced.

For example, this is shown in FIGS. 3a and 3b. Here, the object 16 is displaceable in the longitudinal direction (z), e.g., by means of an object carrier that may also function as the detector 12. Starting from a cone-shaped radiation beam geometry 12_14_b, an increased shielding is provided in the area 19v1 (cf. FIG. 3a).

Assuming a radiation source 14 with a line-geometry 12_14_g', the increased area 19b2 may be further reduced.

Thus, as is shown in FIGS. 3a/b, only the area around the central radiation beam, which is fixed in this direction, of the X-ray source within the gantry is shielded more strongly in the longitudinal direction of the hall, reference numeral 19v2 (cf. FIG. 3b), whereas a basic shielding against diffusive radiation is sufficient for the neighboring areas. In contrast, in the case of the translation of the imaging system, the increased shielding area is multiple times larger, as can be seen in FIG. 3a, reference numeral 19v1.

According to a further embodiment, the design that is optimized with respect to mechanical engineering and radiation protection may also be used for mobile systems since the overall efforts are minimized. Thus, for example, the radiation protection may be assembled from mobile working blocks.

Figure 4A:
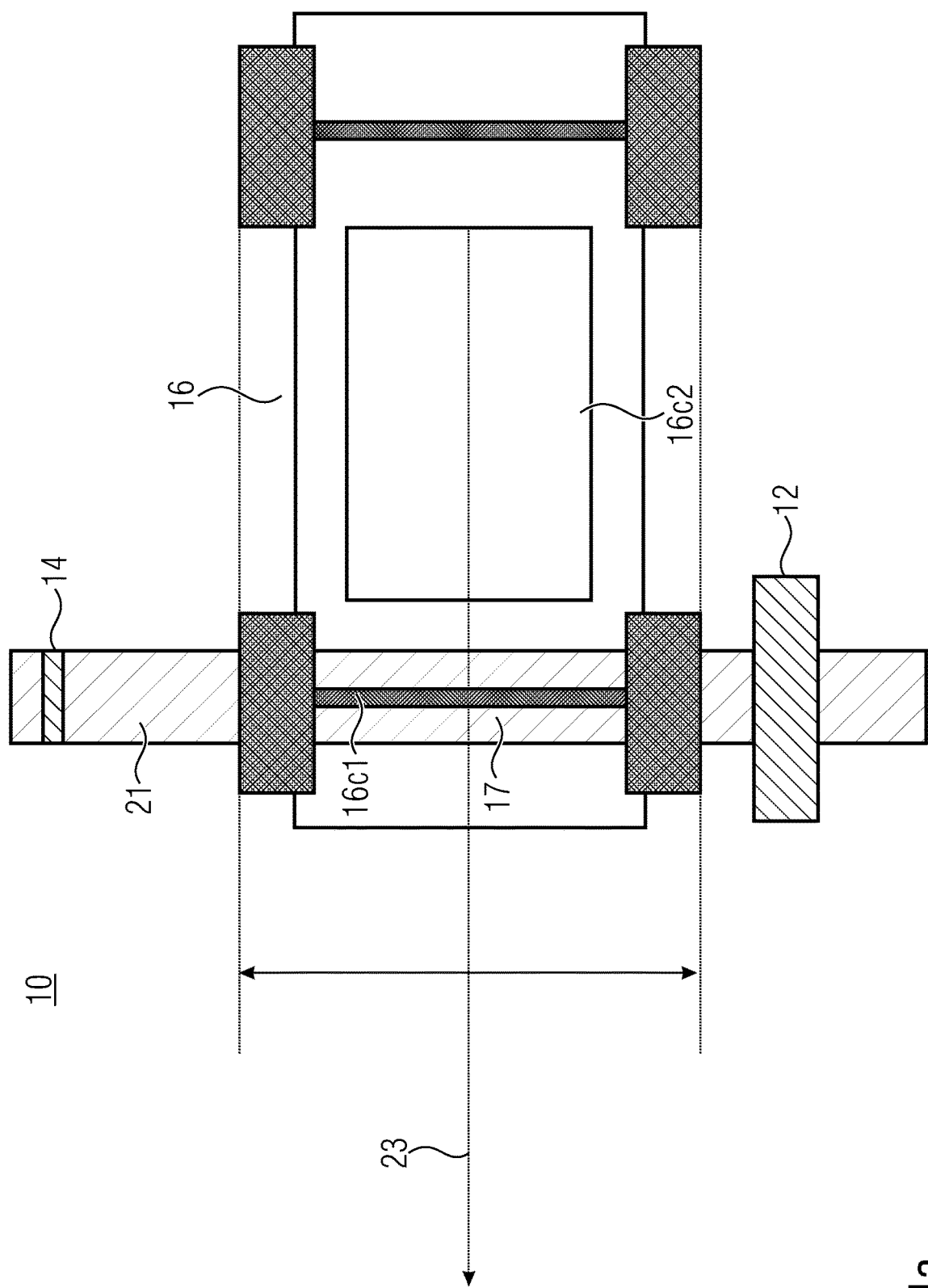

FIG. 4A illustrates the initial situation for a CT system 10 comprising a detector 12 and a source 14 both rotating around the axis 17 and may, as discussed above, be arranged asymmetrically with respect to the rotation axis 17. Note, the asymmetric arrangement is not essential for the recently solved problem, wherein the asymmetrical arrangement enables for the embodiments, which will be discussed with respect to FIG. 4B and FIG. 4C, and the benefits with respect to the resolution. The elements 12 and 14 rotating around the rotation center 17 along a so-called surface of revolution, which is marked by the reference numeral 21. This arrangement can be called gantry.

The object 16, here a car having to access (wherein the first access is marked by the reference numeral 16c1) should be scanned. For doing that, the object 16 is moved along a feed direction 23 through the gantry 21. For example, the feed direction 23 may extend through the rotational center 17. When x-raying the component 16c, here the axis, x-ray using said rotation angle suffer from the problem that the axis is x-rayed along its length direction. Here, no information on the component 16c1 can be gained. This leads to a bad image quality. The same problem can occur when scanning a crank shaft or a longitudinal housing structures i.e. for battery modules (cf. reference numeral 16c2). In order to improve this, the rotational axis 23 is angled, e.g., by the angle α, for example 5°, with respect to the feed direction 23. This can be done by two approaches. According to the first approach, the object 16 is angled on its object holder, wherein the direction 23 is maintained. Alternatively, the entire feed direction 23 is angled with respect to the surface of revolution 21. The angled movement that component 16c1 is x-rayed also in an angled manner, so that more information regarding the object can be gained.

The above-described principle of having an asymmetric arrangement of the elements 12 and 14 with respect to the rotational center 17 is beneficial, since the resolution can be improved. Due to this arrangement, the spacing between the detector 12 and the component 16c is minimized, while due to the spacing between the object 16 and the source 14 enough space for moving the object 16 angled through the gantry 21 is provided. As illustrated by the theoretical position for the detector/radius of the detector 12 (cf. reference numeral 25) the spacing between the detector 12 and the object to be scanned 16c is too large to enable a good resolution. Therefore, the radius 12rr as illustrated by FIGS. 4b and 4c is advantageous.

As can be seen with respect to FIG. 4c, between the detector 12 and the source 14, there is enough space so that an object can be moved through the gantry 21 even when same is angled with respect to the gantry, while a minimum spacing between 12 and 16 is ensured.

According the embodiments, the oblique motion through the gantry for the object 16 can be achieved by providing an angle offered between the perpendicular to the surface of revolution, or by using a movement of the object 16 having two components, one in the x direction and one in the y direction.

According to a further embodiment, a detector with a curved structure may be used, which has an increased efficiency. In this case, the curvature could be implemented section by section on the basis of arranging individual straight modules, or continuously on the basis of arranging individual pixels on the curved trajectory. In this respect, a curved detector or a curved detector with a variable radius of curvature may be used.

According to embodiments, instead of a conventional X-ray tube, a high-energy X-ray source with a radiation energy of >1 MeV (e.g. a line accelerator) is used. According to embodiments, a single detector or a multi-detector, or an area-like detector may be used as a detector, which, due to the size, may image a complete or partial cross section of the object (such as a vehicle).

Subsequently, an embodiment is explained using bullet points. The following is used:
1. A large gantry with a line accelerator and a (multi-) line or area detector.
2. A reduction of the rotation to 180°+opening angle.
3. According to embodiments, an object holder or object carrier may be used for the object.
4. To mount the detector, a smallest possible bearing through which the object passes is used.
5. The placement of the radiation source is carried out on a cantilever by asymmetrical components.

According to embodiments, higher inaccuracy in the positioning of the radiation source side may be accepted. The error position may be compensated in the unit in FIG. 3(b).

This overall concept has the advantage of using small and precise mounts instead of a giant ring, at least for the detector. According to an embodiment, the above-described object holder, or the object stage, is displaced in the z-direction so that spiral computer tomography of the object would be possible.

According to embodiments, the following applications are possible:
1. Motor vehicles—digitalization of vehicles, detection of damages after a crash
2. Aircraft—digitalization
3. Trains—digitalization
4. Large objects of elongated shape
5. Cargo containers—detection of contraband
6. Wind power components—defect analysis
7. Pipe structures Even though a device has been assumed in the above embodiments, it should be noted that a description of a device component may also represent a description of a method step, since at least parts of the explained concept are in the form of method steps. The method may include the basic steps of providing a radiation source and a radiation detector, wherein the radiation source and the radiation detector are arranged with respect to the object such that they are asymmetrical.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, some one or more of the most important method steps may be executed by such an apparatus.

While this invention has been described in terms of several advantageous embodiments, there are alterations, permutations, and equivalents, which fall within the scope of this invention. It should also be noted that there are many alternative ways of implementing the methods and compositions of the present invention. It is therefore intended that the following appended claims be interpreted as including all such alterations, permutations, and equivalents as fall within the true spirit and scope of the present invention.

BIBLIOGRAPHY

[1] M. Salamon, N. Reims, M. Bohnel, K. Zerbe, M. Schmitt, N. Uhlmann and R. Hanke, "XXL CT capabilities for the inspection of modern Electric Vehicles," International Symposium on Digital Industrial Radiology and Computed Tomography, 2019.
[2] S. Zabler, M. Böhnel, N. Reims, M. Salamon and C. Feller, "Industrial X-ray Computed Tomography Scanners," in Handbook of X-ray Imaging: Physics and Technology, CRC Press, 2017.
[3] "HI-SCAN 6040 CTiX," Smith Detection, [Online]. Available: https://www.smithsdetection.com/products/hi-scan-6040-ctix/. [Access on Apr. 2, 2020].
[4] "HCVG Gantry inspection system," Smith Detection, [Online]. Available: https://www.smithsdetection.com/products/hcvg/. [Access on Apr. 2, 2020].
[5] Patent research: US2006/0126772A1

What is claimed is:

1. A CT system, comprising:
an X-ray source; and
an X-ray detector arranged opposite the X-ray source, wherein the X-ray detector and the X-ray source are rotatable around at least one rotation center through a rotator, wherein the distances between the at least one rotation center and the X-ray source and between the at least one rotation center and the X-ray detector differ from each other by at least factor 2;
wherein the X-ray detector (12) is a line detector or an area detector extending tangentially or extending along a rotation circle (12r) of the CT system (10); and
wherein the rotation means comprises a cantilever at which the X-ray source (14) is fixed, wherein the cantilever is rotatable along another rotation circle (14r);
wherein the rotation circle (12r) and the another rotating circle (14r) are concentric and have commonly the rotation center (17);
wherein the rotation means is configured to rotate the X-ray source (14) and the X-ray detector (12) with a limited angle of less than 240°.

2. The CT system according to claim 1, wherein the distances are different to such an extent that an asymmetrical arrangement of the X-ray source and the X-ray detector with respect to an object to be penetrated by radiation arises; and/or
wherein the object is arrangeable between the X-ray source and the X-ray detector such that the at least one rotation center extends through the object to be penetrated by radiation.

3. The CT system according to claim 1, wherein the rotator is configured to rotate the X-ray source and the X-ray detector around 180°, a sum of 180° and fan beam angle, around an angle of between 0° and 120° to 200°, around an angle of between 0° and 150° to 220°, around an angle of between 0° and 120° to 240°.

4. The CT system according to claim 1, wherein the distance between the at least one rotation center and the X-ray source is larger than the distance between the at least one rotation center and the X-ray detector.

5. The CT system according to claim 1, wherein the distances differ at least by the factor 3, or at least by the factor 4.

6. The CT system according to claim 1, wherein the distance between the at least one rotation center and the X-ray detector corresponds to a maximum object cross section of an object to be penetrated by radiation, or to a less than a maximum object cross section of an object to be penetrated by radiation.

7. The CT system according to claim 1, wherein the X-ray detector is a curved line detector or a curved area detector extending along a rotation circle of the CT system.

8. The CT system according to claim 1, wherein the rotator comprises a rigid mount, wherein the rigid mount mounts the X-ray detector along its movement around a rotation circle; and/or
wherein the detector is placed in close proximity to a supporting ring structure of the rotator or directly to the supporting ring structure of the rotator.

9. The CT system according to claim 1, wherein the CT system comprises an object holder or a moveable object holder, wherein the moveable object holder is configured to be moved along a feed direction.

10. The CT system according to claim 1, wherein the CT system comprises an object holder in the form of a stage.

11. The CT system according to claim 9, wherein the object holder is configured to record objects larger than 1×1×1 meters, or larger than 1.5×1.5×1 meters or larger than 2×2×1 meters, or larger than 2×2×2 meters.

12. The CT system according to claim 9, wherein the moveable object holder is configured to be moved along a feed direction which extends perpendicular to an surface of revolution of the X-ray detector and the X-ray source rotatable around the at least one rotation center; or
wherein the moveable object holder is configured to be moved along a feed direction which extends angled by an angle to an surface of revolution of the X-ray detector and the X-ray source rotatable around the at least one rotation center; or
wherein the moveable object holder is configured to be moved along a feed direction which extends angled by an angle to an surface of revolution of the X-ray detector and the X-ray source rotatable around the at least one rotation center; wherein the angle lies in a range between 75° and 90° or between 80° and 85° or between 75° and 89°.

13. The CT system according to claim 12, wherein the feed direction extends through the at least one rotation center.

14. The CT system according to claim 12, wherein the object is arranged along the feed direction such that a component of interest of the object is angled with respect to the surface of revolution.

15. The CT system according to claim 12, wherein a movement of the object holder comprise two components in the space.

16. The CT system according to claim 1, wherein the CT system is mobile.

17. The CT system according to claim 16, wherein the CT system comprises mobile radiation protection blocks.

18. A CT system, comprising:
an X-ray source; and
an X-ray detector arranged opposite the X-ray source, wherein the X-ray detector and the X-ray source are rotatable around at least one rotation center through a rotator, wherein the distances between the at least one rotation center and the X- ray source and between the at least one rotation center and the X-ray detector differ from each other by at least factor 2;
wherein the CT system comprises an object holder or a moveable object holder, wherein the moveable object holder is configured to be moved along a feed direction; wherein the object holder is configured to record objects larger than 1×1×1 meters, or larger than 1,5× 1,5×1 meters or larger than 2×2×1 meters, or larger than 2×2×2 meters.

19. A CT system, comprising:
an X-ray source; and
an X-ray detector arranged opposite the X-ray source, wherein the X-ray detector and the X-ray source are rotatable around at least one rotation center through a rotator, wherein the distances between the at least one rotation center and the X-ray source and between the at least one rotation center and the X-ray detector differ from each other by at least factor 2;
wherein the CT system comprises an object holder or a moveable object holder, wherein the moveable object holder is configured to be moved along a feed direction;
wherein the moveable object holder is configured to be moved along a feed direction which extends perpendicular to a surface of revolution of the X-ray detector and the X-ray source rotatable around the at least one rotation center; or
wherein the moveable object holder is configured to be moved along a feed direction which extends angled by an angle to an surface of revolution of the X-ray detector and the X-ray source rotatable around the at least one rotation center; or
wherein the moveable object holder is configured to be moved along a feed direction which extends angled by an angle to an surface of revolution of the X-ray detector and the X-ray source rotatable around the at least one rotation center; wherein the angle lies in a range between 75° and 90° or between 80° and 85° or between 75° and 89°.

20. A CT system, comprising:
an X-ray source; and
an X-ray detector arranged opposite the X-ray source, wherein the X-ray detector and the X-ray source are rotatable around at least one rotation center through a rotator, wherein the distances between the at least one rotation center and the X-ray source and between the at least one rotation center and the X-ray detector differ from each other by at least factor 2;
wherein the CT system is mobile.

* * * * *